United States Patent [19]

Hanisch et al.

[11] Patent Number: 5,702,699
[45] Date of Patent: Dec. 30, 1997

[54] PROCESS FOR THE RECOVERY OF LIPOPHILIC PROTEINS

[75] Inventors: Wolfgang H. Hanisch, Oakland; Peter Fernandes, Walnut Creek, both of Calif.

[73] Assignee: Cetus Corporation, Emeryville, Calif.

[21] Appl. No.: 474,768

[22] Filed: Jun. 7, 1995

Related U.S. Application Data

[63] Continuation of Ser. No. 103,954, Aug. 10, 1993, abandoned, which is a continuation of Ser. No. 870,155, Apr. 14, 1992, abandoned, which is a continuation-in-part of Ser. No. 592,077, Mar. 22, 1984, abandoned, which is a division of Ser. No. 495,896, May 18, 1983, Pat. No. 4,462,940, which is a continuation-in-part of Ser. No. 422,421, Sep. 19, 1982, abandoned.

[51] Int. Cl.$^6$ ............................................. A61K 38/21
[52] U.S. Cl. ................................. 424/85.6; 530/351
[58] Field of Search ...................... 435/69.1, 172.1, 435/172.3, 320.1, 252.3, 252.33; 530/344, 350, 355, 363, 351; 514/2; 424/85.6

[56] References Cited

U.S. PATENT DOCUMENTS

| | | | |
|---|---|---|---|
| 3,981,991 | 9/1976 | Stewart et al. | 424/85.4 |
| 4,241,174 | 12/1980 | Familletti et al. | 435/5 |
| 4,276,282 | 6/1981 | Sugimoto et al. | 424/85.7 |
| 4,289,689 | 9/1981 | Friesen et al. | 530/351 |
| 4,296,025 | 10/1981 | Sugimoto et al. | 530/351 |
| 4,314,935 | 2/1982 | Uemura et al. | 530/351 |
| 4,315,852 | 2/1982 | Leibowitz et al. | 530/351 |
| 4,343,735 | 8/1982 | Menge et al. | 530/351 |
| 4,343,736 | 8/1982 | Uemura et al. | 530/351 |
| 4,450,103 | 5/1984 | Konrad et al. | 530/351 |
| 4,460,574 | 7/1984 | Yabrov | 424/85.6 |
| 4,462,940 | 7/1984 | Hanisch et al. | 530/351 |
| 4,465,622 | 8/1984 | Nobuhara et al. | 530/351 |
| 4,588,585 | 5/1986 | Mark et al. | 424/85.2 |
| 4,645,830 | 2/1987 | Yasushi et al. | 530/351 |
| 4,647,454 | 3/1987 | Cymbalista | 530/351 |
| 4,659,570 | 4/1987 | Terano | 424/85.5 |
| 4,675,184 | 6/1987 | Haseyawa et al. | 424/85.4 |
| 4,680,175 | 7/1987 | Estis et al. | 424/85.4 |
| 4,714,611 | 12/1987 | Yasaburgo et al. | 424/85.5 |

FOREIGN PATENT DOCUMENTS

| | | |
|---|---|---|
| 0042246 | 12/1981 | European Pat. Off. . |
| 0089245 | 9/1983 | European Pat. Off. . |
| 0133767 | 3/1985 | European Pat. Off. . |
| 59-181224 | 10/1984 | Japan . |
| 8002229 | 10/1980 | WIPO . |

OTHER PUBLICATIONS

Derynck et al. "Expression of Human Fibroblast Interferon Gene in *Escherichia coli*", Nature, vol. 287, 18 Sep. 1980, pp. 193–197.
"Large–Scale Purification of Human Fibroblast Interferon", *Cancer Treatment Reports*, vol. 62, No. 11, Nov. 1978, pp. 1900–1906.
Windholz, et al., The Merck Index, p. 644, monograph 4347 (1983).
Sedmark, et al., Methods in Enzymology, "*Procedures for Stabilizatin of Interferons*", vol. 78, pp. 591–595 (1981).
E. Gross, et al., The Peptides, pp. 39–41 (1983).
Edy, et al., Pro. Soc. Exp. Biol. & Med., vol. 146, pp. 249–253 (1974).
Frank, et al., J. Gen. Virol., vol. 53, pp. 389–392 (1981).
Noda, et al., CA, vol. 102 (1985), No. 154791v.
Hasigawa, et al., CA, vol. 99, No. 76904n.
Kato, et al., CA, vol. 102 (1984), No. 12428h.
Billiau, et al., Antimicrobial Agents and Chemotheraspy, vol. 16(1), pp. 49–55 (1979).

*Primary Examiner*—David Guzo
*Attorney, Agent, or Firm*—Millen, White, Zelano, & Branigan, P.C.

[57] ABSTRACT

An improved process for recovering and purifying lipophilic recombinant proteins such as human β-interferon from their hosts involves concentrating the bacteria; disrupting the cell wall and solubilizing the protein into an aqueous medium with an appropriate solubilizing agent; extracting the protein from the aqueous medium with 2-butanol, 2-methyl-2-butanol or mixtures thereof; precipitating and isolating the protein from the alcohol phase; purifying the protein by chromatography and diafiltering the protein against distilled water or aqueous solutions of ethanol or glycerol at a pH of about 12. Therapeutic formulations of such purified proteins with stabilizers contain SDS levels reduced to less than 10 p.p.m.

14 Claims, 4 Drawing Sheets

PROCESS FOR THE RECOVERY OF LIPOPHILIC PROTEINS

This application is a continuation, of application Ser. No. 08/103,954, filed Aug. 10, 1993, abandoned, which is a continuation of Ser. No. 07/870,155, filed Apr. 14, 1992, abandoned, which is a continuation-in-part of Ser. No. 06/592,077, filed Mar. 22, 1984, abandoned, which is a divisional of Ser. No. 06/495,896, filed May 18, 1983 (U.S. Pat. No. 4,462,940) which is a continuation-in-part of Ser. No.06/422,421, filed Sep. 13, 1982, abandoned.

BACKGROUND OF THE INVENTION

This invention is in the general field of biochemical engineering. More specifically, the subject invention relates to the preparation of biologically active recombinant lipophilic proteins, preferably hyman interferons and interferon-like polypeptides. Still more specifically, the subject invention relates to an improved process for the production and recovery of lipophilic proteins such as human fibroblast interferon and interferon-like polypeptides (β-HIFN) from genetically transformed host organisms, lipophilic protein preparations of relatively high purity, and therapeutically acceptable formulations thereof.

Naturally occurring interferons (IFNs) are species-specific proteins, often glycoproteins, produced by various cells upon induction with viruses, double stranded RNA's, other polynucleotides, antigens and mitogens. Interferons exhibit multiple biological activities such as antiviral, antiproliferative, immunomodulatory and anticellular functions. At least three distinct types of human interferons have been identified and characterized in terms of their anti-viral, anti-growth and activation of natural killer cell (NK) activities. They are produced by leukocytes, lymphocytes, fibroblasts and the immune system and are classified as α, β and γ interferons. These are reported to be different proteins coded for by distinct structural genes.

Since their discovery in 1957, interferons have been extensively and intensively investigated for their potential therapeutic use as antiviral and/or anti-cancer agents. However, the paucity of adequate amounts of the material isolated from natural sources and the expense involved have precluded extensive clinical testing and evaluation of the extent of the therapeutic value of these interferons.

In recent times, however, several of the human interferon genes have been cloned using recombinant DNA technology and expressed in E. coli (Nagola, S. et al., Nature, 284:316 (1980); Goeddel, D. V. et al., Nature, 287:411 (1980); Yelverton, E. et al., Nuc. Acid Res., 9:731 (1981); Streuli, M. et al., Proc. Natl. Acad. Sci. (U.S.), 78:2848 (1981). The expressed proteins or polypeptides have been purified and tested and have been found to exhibit properties similar to those of native IFNs. Bacterially produced IFN's thus appear to have potential therapeutic use as antiviral and anti-tumor agents and the production of IFN's by such bacterial fermentations is expected to yield sufficiently large quantities of IFN at a relatively low cost for clinical testing.

Native human β-interferon (β-HIFN) is generally produced by superinducing human fibroblast cultures with poly-IC (poly-riboinosinic acid and polyribocytidylic acid) and isolating and purifying the β-HIFN thus produced by chromatographic and electrophoretic techniques. Proteins or polypeptides which exhibit native β-interferon like properties may also be produced using recombinant DNA technology by extracting poly-A-rich 12S messenger RNA from virally induced human cells, synthesizing double-stranded c-DNA using the m-RNA as a template, introducing the c-DNA into an appropriate cloning vector, transforming suitable microorganisms with the vector, harvesting the bacteria and extracting the β-HIFN therefrom. European Pat. Application Numbers 28033, published May 6, 1981; 321134, published Jul. 15, 1981; 34307 published Aug. 26, 1981; and Belgian Patent 837397, issued Jun. 1, 1981 describe various currently used methods for the production of β-interferon employing recombinant DNA techniques.

Interferon samples for use in clinical studies, however, must be of relatively high purity and substantially uncontaminated with toxic host cell constituents, cell debris and other extraneous chemicals introduced during the extraction and purification steps. There are several methods currently available for the preparation, recovery and purification of bacterially produced IFNs.

U.S. Pat. No. 4,315,852 to Leibowitz et al. describes and claims a method for the acid extraction of leukocyte interferon from bacterial cells and neutralization of the extractant to obtain the interferon.

Derynck et al., Nature, 287:193 (1980) teach lysing transformed E. coli cells using a solution containing 5M urea, 1% sodium dodecyl sulfate (SDS), and 1% 2-mercaptoethanol. The lysate, which was purified by chromatography, exhibited interferon activity.

Scandella and Kornberg, Biochemistry, 10:4447 (1971) describe the preparation of a phospholipase from E. coli by solubilizing the cell membranes with SDS and precipitating the solubilized protein with 1-butanol.

U.S. Pat. No. 4,343,735, to Menge et al. teaches a process for the purification of interferon by partitioning it in an aqueous multi-phase system in the presence of ion exchangers which are soluble in the system and are derivatives of polyethers.

U.S. Pat. No. 4,343,736 to Uemura et al. discloses a method for recovering interferon by absorption on water-insolubilized heparin and then eluting the interferon with an aqueous solution of an inorganic salt and chondroitin sulfate.

U.S. Pat. No. 4,289,689 to Friesen et al. discloses how to recover and purify human native β-interferon by use of affinity chromatography and high pressure liquid chromatography.

U.S. Pat. No. 4,460,574 to Yabrov discloses a pharmaceutical composition comprising native human α- and β-interferons used for rectal or urogenital treatment of human interferon-sensitive diseases.

U.S. Pat. No. 4,364,863 to Leibowitz et al. describes a method of extracting fibroblast interferon from bacteria using a low pH followed by a high pH extraction procedure.

PCT WO 80/02229 to Benzon discloses purification of alpha (leukocyte) interferon, which is not a lipophilic protein.

EP 42,246 discloses that recombinant interferons may be dissolved in any pharmaceutically acceptable non-toxic carrier appropriate for the desired form of administration without further details.

U.S. Pat. No. 4,450,103 discloses solubilizing the protein in an aqueous medium with an appropriate solubilizing agent, extracting the protein from the aqueous medium with 2-butanol or 2-methyl-2-butanol, and precipitating the protein from the alcohol phase.

Cancer Treatment Reports, 62, 1900–1906 (1978) and EP 89,245 disclose that native beta-interferon may be formulated directly with human serum albumin in a pharmaceutically compatible aqueous-based medium at a pH of 7.2–7.8.

Alpha-interferons and native beta-interferon are not lipophilic proteins. Therefore, they can be stabilized and solubilized by adding a stabilizer such as human serum albumin directly to the formulation at physiological pH. In contrast, lipophilic proteins such as recombinant beta-interferon are not solubilized by addition of human serum albumin at pH 6.8–7.8.

A major problem with the existing methods of purification and recovery of lipophilic proteins is that the protein is not produced in a sufficiently pure form and in sufficiently large quantities for clinical and therapeutic purposes, and further, that the resulting IFN preparations, especially those that are produced by recombinant DNA techniques, have residual toxic amounts of chemicals, such as SDS and other surfactants or precipitants used in the extraction and purification steps. Thus, these preparations are not acceptable for clinical studies designed to determine the extent of the therapeutic use and applications of IFN. It would be desirable, therefore, to have available a process for the recovery of a lipophilic protein such as recombinant β-interferon in sufficiently large quantities and without toxic levels of SDS for clinical and therapeutic applications.

Accordingly, it is an object of the present invention to provide a pharmaceutically acceptable sample of a lipophilic protein such as recombinant β-interferon which is of relatively high purity.

Another object of the present invention is to provide pharmaceutically acceptable samples of lipophilic proteins such as recombinant β-interferon in sufficiently large quantities for clinical and therapeutic applications.

Yet another object of the instant invention is to provide lipophilic proteins such as recombinant β-interferon preparations that are substantially free of SDS without loss of their biological activity, or at levels that are therapeutically acceptable.

A further object of this invention is to provide recombinant β-interferon samples wherein the level of SDS is less than about 10 p.p.m.

SUMMARY OF THE INVENTION

To achieve the foregoing and other objects and in accordance with the purpose of the present invention, as embodied and broadly described herein, one aspect of the invention is an improved method for the production, recovery and purification of a lipophilic protein such as human recombinant β-interferon and comprises solubilizing the protein into an aqueous medium with a suitable solubilizing agent, extracting the solubilized protein with an aliphatic alcohol, precipitating the protein from the alcohol phase with an aqueous buffer, and diafiltering the protein at a pH of about 10.5 to 12.5, preferably at a pH of about 12, against water adjusted to a pH of about 10.5 to 12.5, preferably about 12, or against mixtures of water and aliphatic alcohols, preferably ethanol and glycerol adjusted to a pH of about 10.5 to 12.5, preferably about 12, substantially to remove SDS or to reduce its concentration to therapeutically acceptable levels. The protein sample is optionally purified by conventional methods such as chromatography prior to the diafiltration.

A preferred embodiment of the present invention comprises recovering bacterially produced human β-interferon by disruption of the bacterial cells, solubilization of the interferon with a suitable solubilizing agent, extracting the solubilized interferon with an aliphatic alcohol of 2–6, preferably 4–6, carbon chain length, precipitating the interferon from the alcohol phase, further purifying the interferon by conventional methods, preferably gel filtration chromatography, and diafiltering the interferon fraction at a pH of about 10.5 to 12.5, preferably at a pH of about 11, against pure water or mixtures of water and aliphatic alcohols, preferably methanol, ethanol, propanol, butanol, glycerol and the like, also adjusted to a pH of about 10.5 to 12.5, preferably about 11.

Another aspect of the present invention deals with an improved process for the recovery of human β-interferon and a therapeutic formulation thereof where the levels of SDS are less than about 10 p.p.m.

In another aspect, the therapeutic formulation is a stable pharmaceutical composition comprising a therapeutically effective amount of a biologically active recombinant lipophilic protein dissolved in a non-toxic, inert, therapeutically compatible aqueous-based carrier medium at a pH of 6.8 to 7.8 comprising a stabilizer for the protein.

Preferably, the protein in this latter formulation is β-interferon and the stabilizer is human serum albumin or a mixture of human serum albumin and dextrose.

In a further aspect of the present invention, the therapeutic protein preparation obtained from the diafiltration and stabilization steps may be lyophilized and reconstituted in an inert, non-toxic, physiologically compatible carrier medium for therapeutic and clinical applications.

BRIEF DESCRIPTION OF THE DRAWINGS

FIG. 1 (Parts a–b) illustrates a flow chart of the process steps of the present invention.

DETAILED DESCRIPTION OF THE PREFERRED EMBODIMENTS

As used herein, the term "lipophilic protein" refers to a protein which is not soluble or not readily soluble in an aqueous medium under ambient conditions of room temperature and atmospheric pressure at a pH of between about 6.5 and 7.8. Examples of such proteins include human recombinant β-interferon, recombinant interleukin-2 and immunotoxins prepared by conjugating a cytotoxin moiety such as ricin A to an antibody against a pathologic condition such as breast cancer. The term "recombinant protein" refers to a protein which is produced by recombinant DNA techniques wherein generally DNA is inserted into a suitable expression plasmid which is inserted into a host organism not native to the DNA which is transformed to produce the heterologous protein. The host may be any organism foreign to the DNA such as, e.g., bacteria, yeast, viruses, mammals, etc. Preferably the host is microbial, and most preferably is bacterial.

As used herein, the term "β-HIFN" refers to human β-interferon or β-interferon-like polypeptides produced by recombinant DNA techniques and whose amino acid sequence is the same as or similar or substantially homologous to the unglycosylated and/or glycosylated native β-interferon.

The precise chemical structure of the protein will depend on a number of factors. As ionizable amino and carboxyl groups are present in the molecule, a particular protein may be obtained as an acidic or basic salt, or in neutral form. All such preparations which retain their activity when placed in suitable environmental conditions are included in the definition of proteins herein. Further, the primary amino acid sequence of the protein may be augmented by derivatization using sugar moieties (glycosylation) or by other supplementary molecules such as lipids, phosphate, acetyl groups and the like, more commonly by conjugation with saccharides. Certain aspects of such augmentation are accomplished through post-translational processing systems of the producing host; other such modifications may be introduced in vitro. In any event, such modifications are included in the definition of protein herein so long as the activity of the protein, as defined above, is not destroyed. It is expected, of course, that such modifications may quantitatively or qualitatively affect the activity, either by enhancing or diminishing the activity of the protein in the various assays.

Further, individual amino acid residues in the chain may be modified by oxidation, reduction, or other derivatization, and the protein may be cleaved to obtain fragments which retain activity. Such alterations which do not destroy activity do not remove the protein sequence from the definition.

Finally, modifications to the primary structure itself by deletion, addition, or alteration of the amino acids incorporated into the sequence during translation can be made without destroying the activity of the protein. For example, at least one cysteine residue which is not essential to biological activity, is present in the biologically active protein, and is free to form a disulfide link may be deleted or replaced with another amino acid to eliminate sites for intermolecular crosslinking or incorrect intramolecular disulfide bond formation. Such modified proteins, known as "muteins," are described in U.S. Pat. No. 4,518,584 issued May 21, 1985. In another example, a conservative amino acid of a biologically active protein such as IL-2 or INF-β is substituted for each methionine residue susceptible to chloramine T or peroxide oxidation, wherein additional, non-susceptible methionine residues are not so substituted. A conservative amino acid alteration in this context is defined as one which does not adversely affect biological activity and involves neutral or non-polar amino acid substitutions or deletion of the methionine. In a preferred example of this embodiment the methionine at amino acid position 104 of IL-2 is replaced by an alanine residue.

Preferably the protein herein is β-HIFN. Most preferably the protein is unglycosylated β-HIFN which is produced by a microorganism that has been transformed with a human INF-β gene or a modification of the human INF-β gene that encodes a protein having: (a) an amino acid sequence that is at least substantially identical to the amino acid sequence of native human INF-β and (b) biological activity that is common to native human INF-β. Substantial identity of amino acid sequences means the sequences are identical or differ by one or more amino acid alterations (deletions, additions, substitutions) that do not cause an adverse functional dissimilarity between the synthetic protein and the native human INF-β. Examples of such proteins are the INF-β proteins described in U.S. Pat. No. 4,518,584. Most preferably the INF-β is ser$_{17}$INF-β wherein the cysteine residue at amino acid position 17 is replaced by a serine residue.

As used herein, the term "physiological pH" refers to a pH which is pharmaceutically acceptable to mammals, i.e., a pH of about 7.2–7.6.

As used herein, the term "stabilizer" as applying to the lipophilic protein refers to non-toxic, non-therapeutic, non-immunogenic compositions which act not only to stabilize the diafiltered protein against denaturation and loss of biological activity, but also to solubilize the lipophilic protein in an aqueous medium so that the pharmaceutical formulation constitutes an aqueous solution of diafiltered protein at pH 6.8–7.8 from which the protein will not precipitate. Such stabilizers are not known in the art for their solubilizing function. Examples of such stabilizers include, but are not limited to, proteins or carbohydrates preferably chosen from human serum albumin (HSA), mannitoi, sorbitol, glycerol, dextrose or a mixture thereof, preferably HSA or a mixture of HSA and dextrose.

Many of the methods used for the recovery of lipophilic recombinant proteins, such as bacterially produced β-HIFN, utilize SDS or similar surfactants for the solubilization and isolation of the protein from cellular material and subsequent acid precipitation to obtain the protein. By further purification techniques carried out at or near neutral pH, the SDS levels in the final protein preparations are reduced to about 0.1%, but even these residual levels have been found to be toxic in animal studies and thus qot acceptable for therapeutic or clinical applications. Further removal of SDS by diafiltration techniques in the 4–8 pH range results in almost complete loss of β-HIFN activity due to aggregation and precipitation of the protein. The biological activity of β-HIFN lost during diafiltration may be regained by the addition of SDS.

Figure 4:
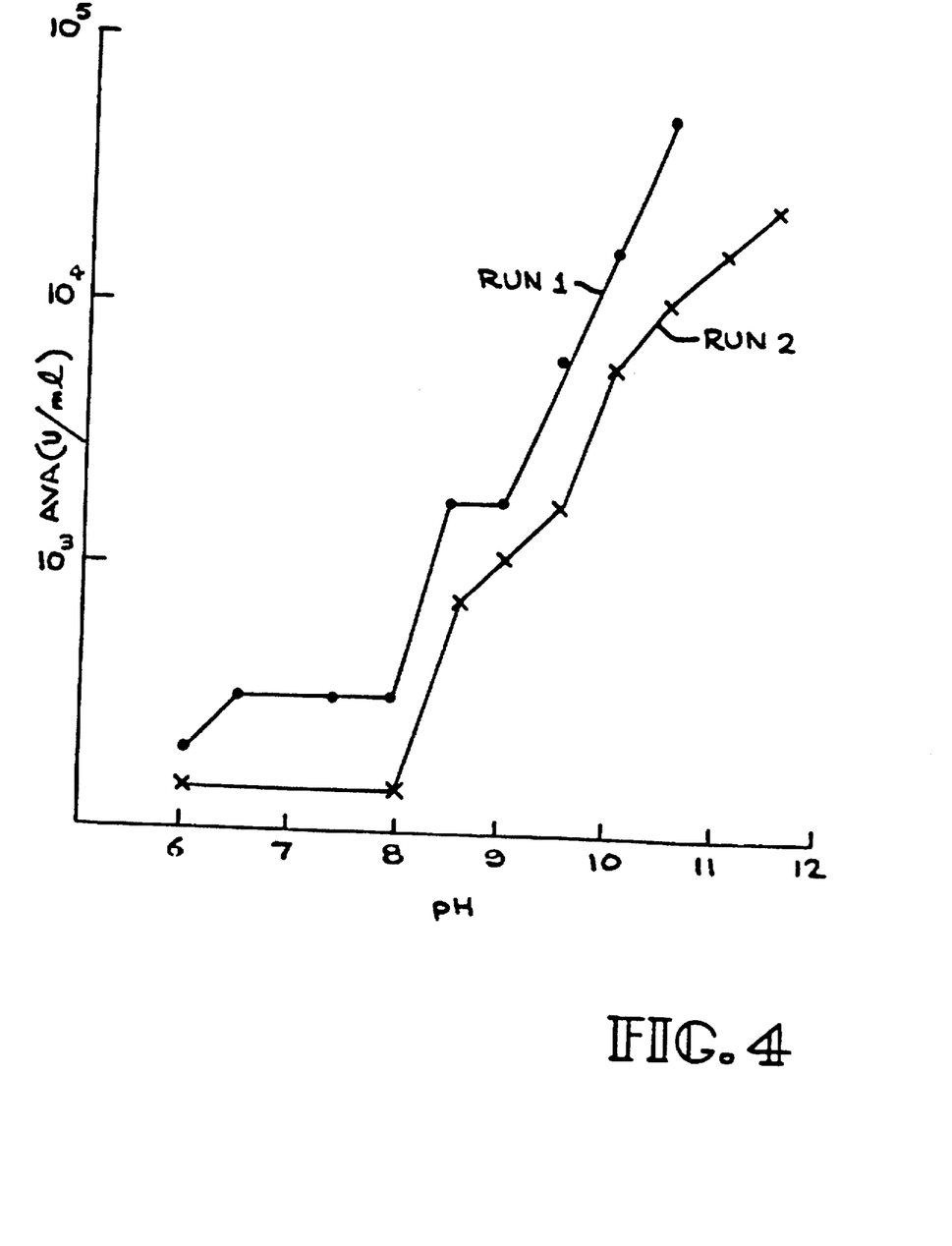
FIG. 4 is a plot of the antiviral activity of recombinant human β-interferon as a function of pH in the range of about 6–12.

For a free or unbund solute, the removal rate during diafiltration from a well mixed vessel follows first order kinetics. Since unbound SDS below its critical micelle concentration is a molecule small enough to pass unhindered through a 10,000 dalton cut-off membrane, its removal rate would be expected to follow first order kinetics, and if that were the case, SDS at an initial concentration of about 1000 µg/ml should be reduced to less than 1 µg/ml after about seven volume replacements. It was found, however, that SDS removal from β-HIFN did not fit this theoretical model, indicating that there were protein-SDS interactions which significantly affected the kinetics of SDS removal, and that SDS removal from this bound state in the 4–8 pH range promoted protein-protein interactions resulting in aggregation or precipitation of the protein. Higher pH ranges for SDS removal would not be expected to be desirable, as at higher pH, some proteins are known to be denatured. However, according to the present invention, following the removal of SDS by diafiltration at low ionic strength, increasing the pH by the addition of sodium hydroxide restores the biological activity of β-HIFN (FIG. 4). The recovery of activity is essentially complete at about pH 12.

Thus, the present invention solves the problem of lipophilic protein (preferably β-HIFN) aggregation and precipitation and loss of protein activity with the removal of SDS by initially adjusting the pH to about 10.5 to 12.5 and diafiltering against distilled water or aqueous mixtures of alcohols, using a 10,000 molecular weight cut-off ultrafiltration membrane after optionally reducing a partially purified sample of the protein with dithiothreitol (DTT) or mercaptoethanol or glutathione or cysteine at about 60° C. and a pH of about 8.5 to prevent aggregation of the protein. Exemplary alcohols include ethanol, butanols, glycerol, mannitol, sorbitol, dextrose and the like.

The subject invention is therefore a process for the recovery of lipophilic recombinant proteins of relatively high purity which contain lower than toxic levels of SDS and which can be reconstituted into therapeutically acceptable formulations in an appropriate carrier medium, and lipophilic protein compositions, more preferably β-HIFN compositions, wherein SDS levels are at less than 10 p.p.m., usually in the range of 2–6 p.p.m.

For purposes of practicing the present invention, bacteria are the preferred microorganism hosts, with *E. coli* being the most preferred.

One preferred embodiment of the process of the instant invention is summarized below.

Figure 1A:
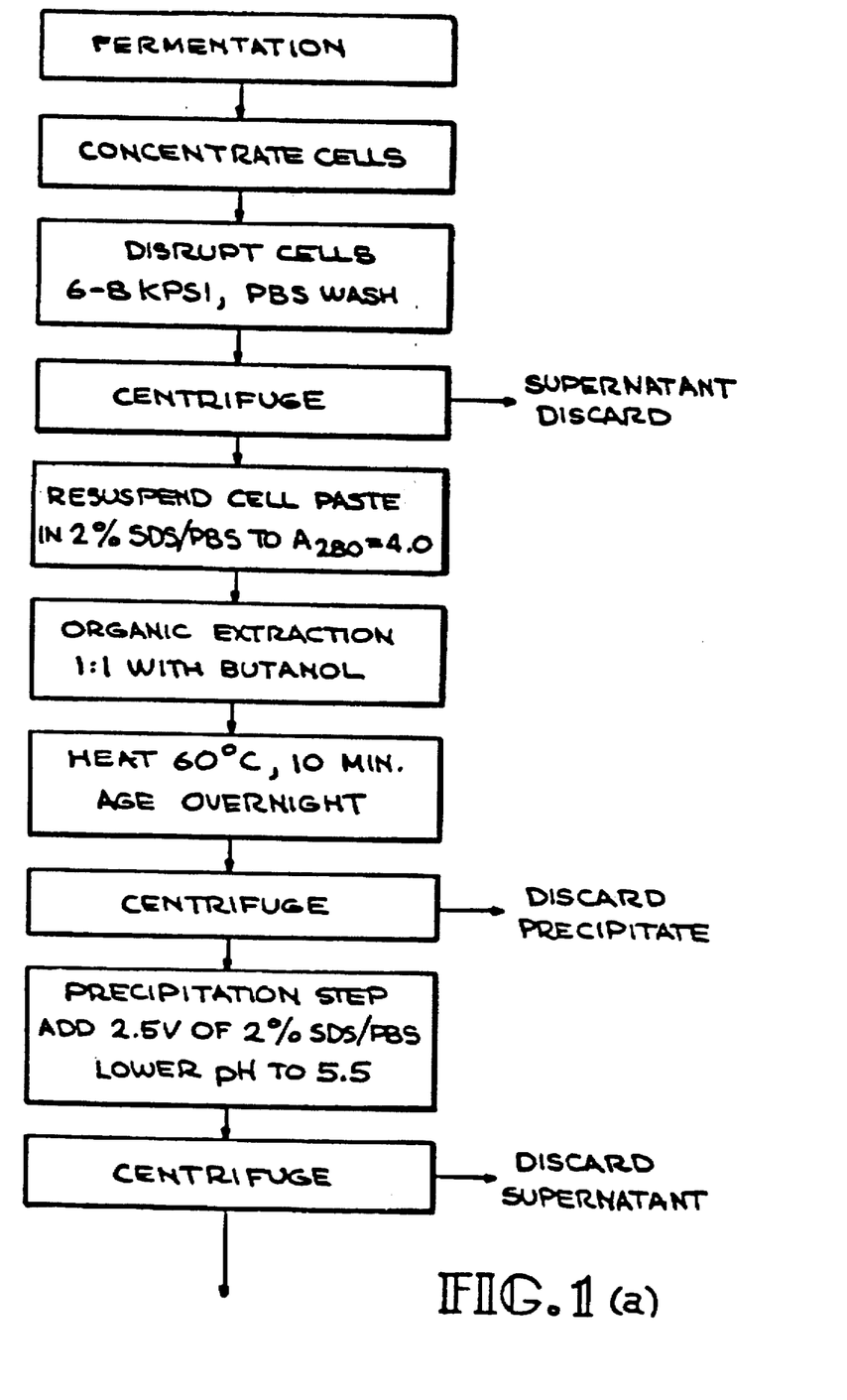
Figure 1B:
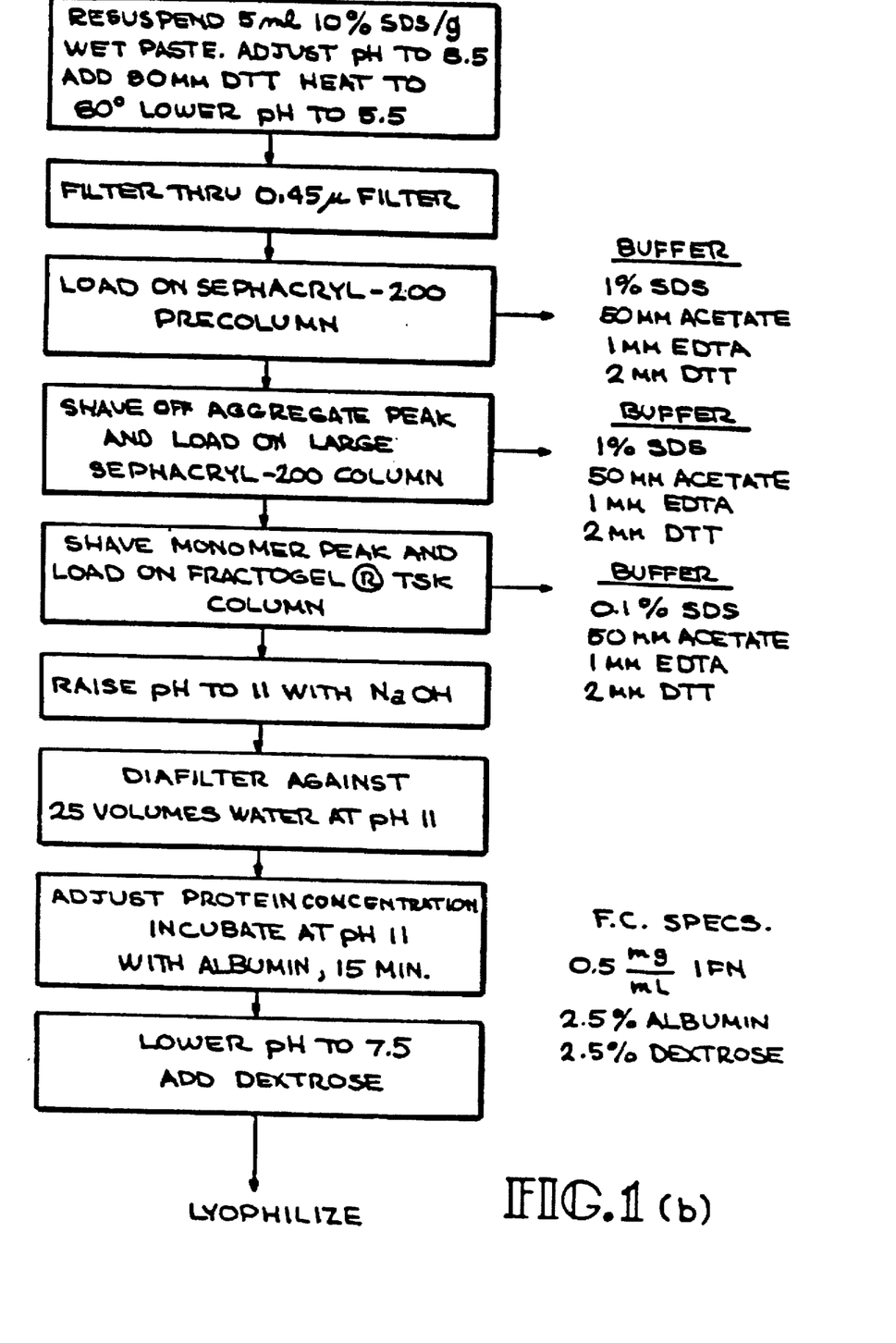

FIG. 1 illustrates the details of the individual process steps of the preferred embodiment of the present invention including the culture of the transformed microorganisms in an appropriate fermentation medium through the final step where the purified β-HIFN is stabilized and may then be lyophilized and reconstituted into therapeutic formulations. The individual process steps include:

growing the transformed bacterial hosts in an appropriate fermentation medium;

concentrating the bacteria in the fermentation medium by cross-flow filtration;

mechanically homogenizing the bacteria to disrupt the cell walls of the bacteria;

separating solid cellular material from the remainder of the homogenate by centrifugation;

solubilizing the solid cellular material by suspending it in an aqueous solution of sodium dodecyl, sulfate (SDS) at a protein to SDS ratio of about 1:3;

extracting the β-HIFN from the aqueous phase with 2-butanol or 2-methyl-2-butanol or mixtures thereof by continuous cocurrent extraction;

heating the 2-butanol or 2-methyl-2-butanol phase to about 60° C. for about 10 to 20 minutes; or aging the 2-butanol phase overnight;

centrifuging the mixture and discarding the precipitated impurities;

contacting the 2-butanol or 2-methyl-2-butanol phase with an aqueous buffer and adjusting the pH of the mixture to about 5.5 to precipitate the β-HIFN;

collecting the precipitated β-HIFN by centrifugation;

solubilizing the β-HIFN with distilled water or with an aqueous solution of SDS at a protein to SDS ratio of about 1:3;

adjusting the pH of the solution to about 9.5 and reducing the solubilized β-HIFN with dithiothreitol;

purifying the reduced β-HIFN by chromatography;

collecting the eluted fraction of the purified β-HIFN;

further purifying the β-HIFN by gel chromatography;

collecting the eluate containing the purified β-HIFN;

adjusting the pH of the eluate to about 12;

diafiltering the solution containing the β-HIFN at a pH of about 11 against pure water or $H_2O$-ethanol mixtures adjusted to a pH of about 11;

adjusting the pH of the diafiltrate to about 12 and stabilizing (and thereby solubilizing) the β-HIFN by the addition of a 0.5–10% by weight solution of dextrose and human serum albumin adjusted to a pH of about 12, and maintaining a pH of 12 for 1–15 minutes;

adjusting the pH of the solution down to physiological pH;

lyophilizing the β-HIFN sample, if desired; and reconstituting the lyophilized β-HIFN sample, if desired.

Ten mM dithiothreitol may be optionally included in the initial solubilization step and the mixture may be heated to about 90° C. for about 10 minutes.

Generally, proteins are susceptible to denaturation, peptide bond hydrolysis, hydrolysis of individual amino acids, β-elimination, racemization, formation of different amino acids and similar reactions in the high alkaline pH range; but with β-HIFN, none of the degradative reactions enumerated above are detected. On the other hand, when the protein is diafiltered at a pH of about 11, the resulting β-HIFN is pure and homogeneous and exhibits high specific activity, close to that of native β-HIFN.

The transformed microorganisms are grown in a suitable growth medium, typically to an optical density (OD) of at least about 10 at 680 nm, and preferably between about 50 and 100 at 680 nm. The composition of the growth medium will depend upon the particular microorganism involved. The aqueous growth medium contains compounds that fulfill the nutritional requirements of the microorganism of choice. Growth media will typically contain assimilable sources of carbon and nitrogen, energy sources, magnesium, potassium and sodium ions, and optionally amino acids and purine and pyrimidine bases. (Review of Medical Microbiology, Lange Medical Publications, 14th Ed. pp. 80–85 (1980).) Growth media for *E. coli* are well known in the art. Depending upon the particular solubilizing agent used in the invention process it may be desirable to minimize the amount of substances in the growth medium that may decrease the solubility of the solubilizing agent in water. For instance, potassium ions affect the solubility of SDS and, therefore, should be kept to a minimum when SDS is used as a solubilizing agent in the process, or removed by diafiltration following the concentration step.

Once the culture has reached the desired cell density, the cells are optionally killed or inactivated by heating or adding to the medium a cytotoxic agent such as chloroform or toluene that may be removed easily after the cells have been killed. The cells are thereafter optionally concentrated to about 20 to 150 mg/ml, preferably 80 to 100 mg/ml (OD 40 to 300, preferably 160 to 200 at 680 nm), by cross-flow filtration, centrifugation, or other conventional methods.

Following the concentration step, the cell membranes of the microorganisms are disrupted to facilitate the solubilization of the particulate matter in the concentrate. β-HIFN assays for biological activity indicate that much of the interferon is associated with (i.e., contained in or bound to) the cell membrane. Accordingly, disruption of the cell membrane enhances the contact of the solubilizing agent with the membranes and thus increases the rate at which the interferon associated with the membrane goes into solution. Conventional cell disruption techniques such as homogenization, sonication, or pressure cycling may be used in this step of the process. A preferred method is using a bead mill or a pressure homogenizer. Either before or after the disruption, the pH of the liquid phase of the concentrate or disruptate, as the case may be, is adjusted, if necessary, to a level that facilitates dissolution of the solubilizing agent and the particulate matter in the concentrate/disruptate. The pH may be so adjusted by adding suitable buffers or with NaOH. In most instances a pH in the range of about 7 to about 8 is preferred.

After the cells have been disrupted the particulate matter can be separated from the liquid phase of the disruptate and resuspended in an aqueous medium buffered to the optimal pH for solubilization. The protein concentration of the cell suspension after solubilization is in the range of about 2 to about 15 mg/ml, preferably 6 to 8 mg/ml.

The solubilization of the particulate cellular material, including the lipophilic recombinant protein, can be carried out concurrently with the disruption or sequentially following the disruption. It is preferably carried out as a separate step following the disruption. The solubilization is preferably carried to completion—that is, substantially all of the particulate matter (e.g., protein, lipids, nucleic acids, phospholipids) in the disruptate is dissolved into the aqueous medium. Substantially complete dissolution of the particulate matter is achieved by adding an appropriate solubilizing agent to the aqueous suspension. Surfactants (detergents) that have a suitable hydrophobic-hydrophilic balance to solubilize β-HIFN and which form a complex with β-HIFN which can be extracted into the organic phase can be used in the invention. Strong natural or synthetic anionic surfactants such as alkali metal salts of fatty acids and alkali metal alkyl sulfates may be used. Such agents will usually contain 10 to 14 carbon atoms. SDS and sodium laurate are particularly preferred solubilizing agents. Examples of other solubilizing agents that can be used in the process include, but are not limited to, sodium dodecyl sulfonate, sodium decyl sulfate, sodium tetradecyl sulfate, sodium tridecyl sulfonate, sodium myristate, sodium caproylate, sodium dodecyl N-sarcosinate, and sodium tetradecyl N-sarcosinate.

The amount of solubilizing agent used in the solubilization depends upon the particular agent and the amount of protein to be solubilized. In most instances, solubilizing agent to protein weight ratios in the range of about 1:1 to 10:1 are sufficient. When SDS is used, an SDS to protein ratio of about 1:1 to about 5:1, preferably about 3:1, is used. Temperatures in the range of 15° C. to 60° C. are generally used in the solubilization. Mixing may be employed to enhance contact between the solution and particulate matter and thus decrease the time it takes to dissolve the cellular matter. The solubilization is considered complete when the solution is substantially clear. Optical densities of about 4.0 to 8.0 at 280 nm are characteristic of the end point of the solubilization process.

Following the solubilization, the ionic strength of the solution is adjusted, if necessary, to a level at which the solution and organic extractant are substantially immiscible. The ionic strength is in the range of about 0.05 to 0.15. Inorganic salts, including NaCl and/or the like, are added to the solution for this purpose. Such ionic strengths enable phase separation after the extraction. The extractants used in the process are alcohols such as 2-butanol, 2-methyl-2-butanol, or mixtures thereof. The mixtures preferably contain less than about 50% by volume of 2-methyl-2-butanol. 2-Butanol is the preferred extractant. The ability of these alcohols to extract the lipophilic protein from the solubilizate is specific. The extractant is noramlly combined with the aqueous solution of the protein in volume ratios in the range of about 0.8:1 to about 3:1, preferably about 1:1 (extractant:aqueous solution). The extraction can be carried out using conventional batch or continuous liquid-liquid extraction techniques and equipment. The extraction is normally carried out at about 20° C. to 100° C. and involves contact times in the range of about one minute to one hour. The optimum contact time depends upon the particular solubilizing agent and extractant combination. When SDS is used, shorter times in the above range can be used. When sodium laurate is used, longer times in the range must be used. The pH of the extraction mixture ranges between about 6 and 9, with a pH of about 7.5 being preferred when SDS is used, and a pH of about 8.5 when sodium laurate is used.

Figure 2:
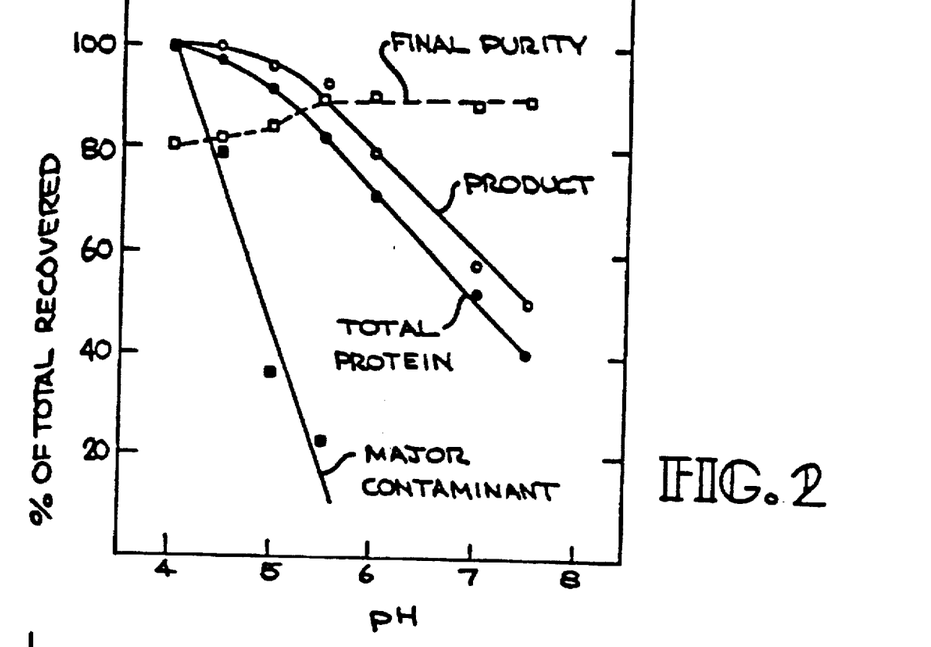
FIG. 2 shows a graph plotting percentage of the total recovery of recombinant human β-interferon and purity of the product during the precipitation step, as a function of pH in the range of about 4–8.

Upon completion of the extraction, the aqueous phase and extractant phase are separated and the protein is isolated from the extractant phase. The particular isolation procedure used depends upon the solubilizing agent involved and the desired degree of purity of the final product. Various isolation techniques such as precipitation, molecular sieve chromatography, affinity chromatography, and electrophoresis may be employed. In instances in which SDS is used, the desired lipophilic protein together with other proteins are precipitated from the extractant by mixing the extractant solution with aqueous buffer at volume ratios of about 2.0:1 to about 5:1, preferably about 3:1, and reducing the pH, typically to the range of about 5 to 7. The recovery of β-HIFN in the range of the pH 4 to 8, as shown in FIG. 2, shows a downward trend in the recovery of the protein with increasing pH, with an appreciable loss in the recovery of greater than 60% at a pH of about 8. Separation of the precipitate from the supernatant and evaporation of residual extractant from the precipitate provide a product that is greater than about 90% pure protein provided that the pH of the precipitation step is greater than 5.5. This product also contains minor amounts of nucleic acids (<1% to 2% by weight) and SDS (<1% w/v). After further purification by methods known in the art, including but not limited to, chromatography, SDS is removed by diafiltration at a pH of about 10.5 to 12.5, preferably about 12. The second purification step is optional and is not required for SDS removal by diafiltration. When sodium laurate is used as a solubilizing agent it precipitates from the extractant together with the protein on lowering the pH. Sodium laurate is extracted from the protein using organic solvents such as acetone, methanol and the like. Prior to diafiltration, the protein may be optionally reduced with appropriate reducing agents. Mercaptoethanol, glutathione, cysteine and dithiothreitol (DTT) may be employed for this purpose, with DTT being the most preferred.

The protein thus isolated is then solubilized in an aqueous-based carrier medium using a stabilizer as described above. The stabilizer, however, cannot merely be mixed with the protein for solubilization to occur. First the pH of the stabilizer must be raised to between 10.5 and 12.5 using a suitable base, preferably about 12, then the stabilizer is added to the diafiltered protein pool which is at pH 10.5-pH 12.5, and finally the pH of the resulting formulation is lowered to between about 6.8 and 7.8. Upon lowering the pH, the protein becomes solubilized in the medium.

The carrier medium used for the formulation for therapeutic or clinical administration may be any non-toxic, inert and aqueous-based vehicle such as those commonly used to formulate pharmaceuticals for animal or human administration. The carrier also is selected so that it does not affect the biological activity of the lipophilic protein.

Examples of such carriers include distilled water, physiological saline, Ringer's solution, dextrose solution, and Hank's solution. The same carriers can be used to reconstitute lyophilized lipophilic protein.

The process of the present invention is further described by the following examples. These examples are provided for purposes of illustration only and are not intended to limit the invention in any manner.

EXAMPLE 1

Cell Production and Harvest

Human β-HIFN was recovered from *E. coli* that had been transformed to produce β-HIFN. The *E. coli* were grown in the following growth medium to a cell density (OD) of 10–11 at 680 nm (dry wt 10 g/l).

| Ingredient | Concentration |
| --- | --- |
| $NH_4Cl$ | 20 mM |
| $K_2SO_4$ | 16.1 mM |
| $KH_2PO_4$ | 7.8 mM |
| $Na_2HPO_4$ | 12.2 mM |
| $MgSO_4.7H_2O$ | 3 mM |
| $Na_3$ citrate.$2H_2O$ | 1.5 mM |
| $MnSO_4.4H_2O$ | 30 μM |
| $ZnSO_4.7H_2O$ | 30 μM |
| $CuSO_4.5H_2O$ | 3 μM |
| L-tryptophan | 70 mg/l |
| $FeSO_4.7H_2O$ | 72 μM |
| thiamine.HCl | 20 mg/l |
| tetracycline | 10 mg/l |
| glucose | 40 g/l |

The pH was controlled with $NH_4OH$.

The bacteria were then harvested and concentrated in a hollow-fiber cross-flow filtration system, using microporos polypropylene fiber system with an internal diameter (I.D.) of about 0.3 mm and a recirculation rate of about 3.5 gpm/cartridge.

EXAMPLE 2

Cell Disruption

The cells, at a final concentration of 9–10% (w/v), were mechanically disrupted by means of a Manton-Gaulin type homogenizer (Gray, P. P. et al., *IV IFS: Ferment Tech. Today*, 347–351 (1972)), fitted with a special valve. A single pass at 6–10,000 psig pressure drop yielded greater than 90% cell disruption. The cells were subjected to three passes to obtain maximum disruption without losing β-HIFN activity and to shear nucleic acids to reduce viscosity.

EXAMPLE 3

Centrifugation Of Homogenate

The homogenized cell material was diluted 1:1 (v/v) with phosphate buffered saline (PBS) at a pH of about 7.4 to give a final volume of two liters. This material was continuously centrifuged at 12,000×g at a flow rate of about 50 ml/min. The solid material was separated from the supernatant and resuspended in four liters of PBS containing two percent by weight of SDS. This suspension was stirredaat room temperature for 15 minutes, after which there was no visible suspended material. The solution was then extracted with 2-butanol at a 1:1 volume ratio of 2-butanol to solution. The extraction was carried out in a liquid-liquid phase separator using a combined flow rate of about 200 ml/min. The organic phase was then separated and evaporated to dryness to yield 21.3 g of protein. This was resuspended in distilled water at a 1:10 volume ratio.

Figure 3:
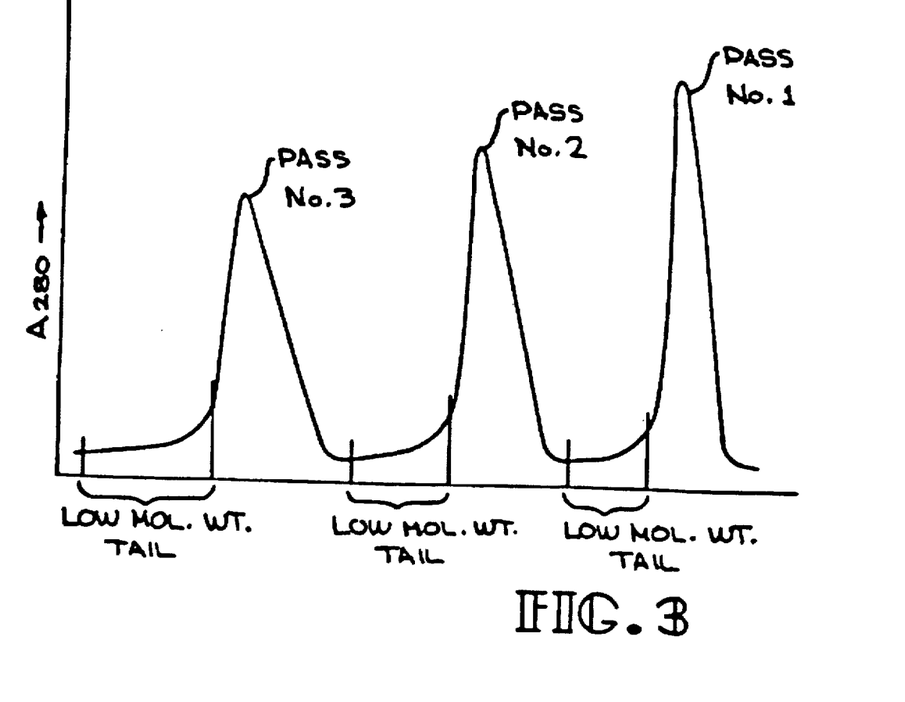
FIG. 3 is a representation of a chromatographic chart illustrating the homogeneity of the recombinant human β-interferon fraction eluted after three passes through a vinyl polymer gel column.

The recovered product was assayed for β-HIFN using an assay based on protection against viral cytopathic effect (CPE). The assay was made in microtiter plates. Fifty μl of minimum essential medium were charged into each well and 1:3 volume dilutions were made serially into the following wells. Virus (vesicular stomatitis), cell (human fibroblast line GM-2504), and reference β-HIFN controls were included on each plate. The reference β-HIFN was 100 units per ml. The plates were then irradiated with UV light for 10 minutes. After irradiation 100 pl of the cell suspension ($1.2\times10^5$ cells/ml) was added to each well and the trays were incubated for 18–24 hours. A virus solution at one plaque-forming unit per cell was added to each well except to the cell control. The trays were then incubated until the virus control showed 100% CPE. This normally occurred 18–24 hours after adding the virus solution. Assay results were interpreted in relation to the location of the 50% CPE well of the reference β-HIFN control. From this point the titer of interferon for all samples on the plate was determined. The activity of the recovered product was determined to be $2.9\times10^6$ IU/mg.

EXAMPLE 4

Extraction of β-HIFN

A 10 liter tank was harvested (9.8 kg) and concentrated to 2.2 liters by cross-flow filtration. The slurry was frozen and stored for 34 days and then thawed.

The thawed concentrate was disrupted by three passes at $7\times10^4$ kPa in a Manton-Gaulin type homogenizer. The disruptate was collected and made up to 4 liters with a solution of sodium laurate to give a final concentration of 1% w/v laurate. The pH was adjusted to 8.5 with 10% NaOH. The solution was contacted with a mixture of 50 vol % 2-butanol and 50 vol % 2-methyl-2-butanol in a static mixer. The emulsion was pumped into a holding tank and agitated to give a contacting time of 15 minutes. This emulsion was separated as described in Example 3 and the β-HIFN recovered in the organic phase. The activity recovered was 16% of the initial value with a specific activity (determined as in Example 3) of $3.7\times10^5$ IU/mg protein.

EXAMPLE 5

Acid Precipitation of β-HIFN

The process of Example 4 was repeated except that after extraction and separation of the aqueous and organic phases the organic phase was mixed with PBS or 10 mM phosphate buffer at a pH of about 7.4 at a volume ratio of 3:1. The pH of the mixture was lowered to about 5.5 by the addition of glacial acetic acid. The resuting precipitate was separated by centrifugation at 10,000–17,000×g for 15 minutes and the pellet was redissolved in 10% w/v SDS.

The precipitate was applied to a molecular sieve column with a Sephacryl S-200® Superfine matrix. The column was equilibrated with 50 mM sodium acetate buffer at pH 5.5 containing 2 mM DTT and 1.0% SDS (w/v). The column was developed with the same buffer at a flow rate of 5 ml per $cm^2$ per hour. Protein profile was monitored at 280 nm with a UV spectrophotometer. Fractions collected were assayed for protein content by methods known in the art. The interferon concentration was determined by the CPE assay as described in Example 3. Degree of interferon purity was determined by SDS polyacrylamide gel electrophoresis (PAGE). Fractions containing the highest interferon activities were pooled and the specific activity of the pooled interferon preparation was determined to be $1–2\times10^7$ IU/mg protein.

EXAMPLE 6

Final Chromatography

The process of Example 5 was continued by concentrating the pool from the Sephacryl-200 step ten fold using a 10,000 nm wt. (nominal molecular weight) cut-off filter and then applying the material to a fine vinyl polymer gel column. This colunn was equilibrated with 50 mM sodium acetate buffer at pH 5.5 containing 2 mM dithiothreitol and 0.1% SDS (w/v). The column was developed with the same buffer at a flow rate of 15.6 ml/cm²/hr. The protein profile was monitored at 280 nm with a spectrophotometer, the protein peak was recycled three times prior to being collected, and fractions were assayed for protein activity and purity by SDS-PAGE. FIG. 3 depicts the eluate peaks after the first, second and third passes as monitored by the protein (β-HIFN) concentration plotted as O.D. vs. eluate fractions exhibiting protein absorption at 280 nm. The peak area after each pass remained substantially the same, indicating that there was no protein loss and that the preparation remained substantially homogeneous after three passes. Fractions containing the highest interferon assay by the cytopathic effect assay were pooled. Specific activity of the pool was in the range of $1-2 \times 10^7$ IU/mg protein.

EXAMPLE 7

Removal Of Residual Reagents

The pH of the pool collected in Example 6 above was raised to pH 12 and placed in a diafiltration device. This protein was reduced by treatment with 10 mM dithiothreitol (DTT) at pH 8.5 prior to raising the pH of the pool to 12 with 2.5M sodium hydroxide. Reduction with DTT was optional and may be omitted if desired.

Diafiltration was carried out at 1 mg/ml protein using a hollow fiber ultrafiltration cell equipped with a 1 sq. ft. surface area (10,000 dalton cut off) cartridge. The pool was diafiltered against 20 volume exchanges of water with the pH adjusted to 12 with 2.5M sodium hydroxide. Sodium dodecyl sulfate levels were monitored and residual levels were found to be less than 10 p.p.m. Residual DTT, EDTA and other low molecular weight species were undetectable. The specific activity of the protein following diafiltration was unchanged from that prior to diafiltration. As shown in FIG. 4, the antiviral activity of β-HIFN following diafiltration was not lost even at a pH of 12.

EXAMPLE 8

Formulation With Human Serum Albumin/Dextrose

The diafiltered interferon (β-HIFN) from Example 7 was diluted to 0.25 mg/ml and incubated with pharmaceutical grade human serum albumin (final concentration 1.25% w/v.) for 15 minutes at pH 12. The pH of the solution was then lowered to 7.5±0.3 with dilute hydrochloric acid, and pharmaceutical grade dextrose was added to a final concentration of 1.25% w/v. The pool was then sterile filtered through an absolute 0.2 μm filter. Specific activity of the formulated material was $1-2 \times 10^7$ IU/mg interferon.

When 10% HSA at its unadjusted pH level was added to the recombinant β-HIFN diafiltered concentrate from Example 7 which was at pH 11.5, the β-HIFN precipitated from the solution when the pH of the mixture was lowered to physiological pH. Only when the HSA and β-HIFN were both adjusted to pH 11.5 before mixing did the β-HIFN remain in solution when the pH of the formulation was reduced. Therefore, the formulation where recombinant β-HIFN is dissolved in the medium at pH 7.2–7.8 is obtained only by following a very specific pH adjustment procedure not previously known or disclosed.

In another experiment, β-HIFN with a serine residue substituted for a cysteine residue at, position 17 prepared by the process described in U.S. Pat. No. 4,518,584 issued May 21, 1985 was purified on a G-75 Sepharose column. The G-75 pool comprised 50 mM acetate buffer at pH 5.5 containing 0.1% SDS and 1.88 mg/ml of the interferon. The actual concentration of SDS was 0.3–0.6 mg/ml. This pool was mixed in test tubes with 0.4, 0.8 or 1.2 ml of HSA. The final pH range of each formulation was 6.8–7.2, and the same results would occur if the final pH were increased up to 7.8. In each case the interferon precipitated from the formulation. Therefore, the lipophilic protein cannot merely be mixed with HSA as a stabilizer at a pH of 6.8–7.8.

EXAMPLE 9

Lyophilization And Reconstitution

The sterile formulated interferon pool was filled in 4 ml aliquots and lyophilized using the following cycle.

1. Product at −35° C., <100 millitorr for at least 1 hour.
2. Product at −20° C., <100 millitorr for at least 1 hour.
3. Product at +25° C., <100 millitorr for at least 4 hours.

The vials were then sealed under 10" Hg vacuum.

The product was reconstituted in distilled water for injection to either 0.5 mg IFN/ml or 1 mg IFN/ml. Specific activity of the product corresponded to $0.9-1 \times 10^7$ IU/mg β-HIFN.

The process and compositions of the present invention as described herein yield a lipophilic protein preparation which is of relatively high purity, with residual SDS levels of less than about 10 p.p.m. and which may be formulated into therapeutically acceptable preparations in a non-toxic, inert, physiologically compatible carrier medium for clinical and therapeutic uses. The principal advantage of the instant invention lies in the reduction of SDS levels in the protein preparation to about 2–20 p.p.m., preferably to less than about 10 p.p.m., and more preferably to about 2–6 p.p.m., which are therapeutically acceptable. Although the preferred embodiment described relates to β-HIFN specifically, the diafiltration method of the instant invention can be used to purify other proteins with similar lipophilic characteristics to β-HIFN.

The foregoing description of the preferred embodiments of the instant invention has been presented for purposes of illustration and description. It is not intended to be exhaustive or to limit the invention to the precise form disclosed, and obviously many modifications and variations are possible in light of the above teaching. The particular embodiments were chosen and described to explain best the principles of the invention and its practical application thereby to enable others skilled in the art to utilize best the invention in various embodiments and with various modifications as are suited to the particular use contemplated. It is intended that the scope of the invention be defined by the claims appended hereto.

What is claimed is:

1. A pharmaceutical composition comprising a therapeutically effective amount of unglycosylated recombinant human interferon-β (IFN-β) dissolved in a non-toxic, therapeutically compatible aqueous-based carrier medium comprising as a stabilizer at pH of 6.8 to 7.8 wherein said stabilizer comprises human serum albumin wherein the composition is produced by a process comprising:

1) recovering the recombinant human IFN-β from a bacterial host transformed to produce it;
2) isolating and purifying the recombinant human IFN-β in a solution containing a solubilizer;
3) adjusting the pH of the solution to about 10.5 to 12.5;
4) diafiltering the solution at a pH of about 10.5 to 12.5 against pure water or water/aliphatic alcohol mixtures adjusted to a pH of about 11 to remove free or IFN-β-bound solubilizer.

5) adding an aqueous-based carrier medium of a pH of about 10.5 to 12.5 to the diafiltered solution containing the recombinant human IFN-β;

6) maintaining the resulting solution at a pH of about 10.5 to 12.5 for 1 to 15 minutes;

7) lowering the pH of the resulting solution to between about 6.8 and 7.8;

wherein the pharmaceutical composition contains less than 10 ppm of solubilizer when the solubilizer is sodium dodecyl sulfate, and wherein the stabilizer in the aqueous-based carrier medium is effective to stabilize the recombinant human IFN-β against denaturation and loss of biological activity and to prevent precipitation of the recombinant human IFN-β from aqueous-based carrier medium.

2. The composition of claim 1 wherein the human serum albumin is present in concentration range of about 0.5 to 10% (w/v).

3. The composition of claim 1 wherein the stabilizer is a mixture of human serum albumin and dextrose.

4. The composition of claim 1 wherein the solubilizer is sodium dodecyl sulfate (SDS).

5. The composition of claim 1 wherein the therapeutically effective amount of recombinant human IFN-β is in the range of 0.1 to 1.0 mg recombinant human IFN-β/mL of aqueous-based carrier.

6. The composition of claim 1 wherein the level of sodium dodecyl sulfate is in the range of about 2 to 6 ppm.

7. The composition of claim 1 wherein the aqueous-based carrier medium is selected from the group consisting of physiological saline solution, distilled water, Ringer's solution and Hank's solution.

8. The composition of claim 1 wherein the recombinant human IFN-β is $ser_{17}$IFN-β.

9. The composition of claim 1 wherein the specific activity of the recombinant human INF-β is in the range of $1-2\times10^7$ IU/mg recombinant human INF-β.

10. The composition of claim 1 wherein the bacterial host is E. coil bacteria.

11. The composition of claim 3 wherein the human serum albumin and the dextrose are each present in the amount of 1.25% (w/v).

12. The composition of claim 8 wherein the composition is lyophilized.

13. The composition of claim 9 wherein the therapeutically effective amount of recombinant human INF-β is in the range of 0.1 to 1.0 mg recombinant human IFN-β/mL of aqueous-based carrier, the stabilizer is human serum albumin, the solubilizer is sodium dodecyl sulfate present at a level of 2 to 6 ppm, and the aqueous-based carrier is selected from the group consisting of physiological saline solution, distilled water, Ringer's solution and Hank's solution.

14. The composition of claim 12 which is reconstituted in an aqueous-based carrier medium at a concentration equivalent to the prelyophilization concentration, wherein the reconstituted concentration of recombinant human IFN-β is therapeutically effective and the recombinant human IFN-β is substantially fully recovered in soluble and biologically active form.

* * * * *